(12) United States Patent
Nomura et al.

(10) Patent No.: US 11,553,964 B2
(45) Date of Patent: Jan. 17, 2023

(54) OPTICAL PROBE, MEDICAL LASER PROBE, AND CAUTERIZATION DEVICE

(71) Applicant: FURUKAWA ELECTRIC CO., LTD., Tokyo (JP)

(72) Inventors: Yoshiki Nomura, Tokyo (JP); Kengo Watanabe, Tokyo (JP); Shunichi Matsushita, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 16 days.

(21) Appl. No.: 17/190,715

(22) Filed: Mar. 3, 2021

(65) Prior Publication Data

US 2021/0177516 A1    Jun. 17, 2021

Related U.S. Application Data

(63) Continuation of application No. PCT/JP2019/035404, filed on Sep. 9, 2019.

(30) Foreign Application Priority Data

Sep. 10, 2018 (JP) .............................. JP2018-168431

(51) Int. Cl.
*A61B 18/24* (2006.01)
*G02B 6/34* (2006.01)
*A61B 18/00* (2006.01)

(52) U.S. Cl.
CPC ............... *A61B 18/24* (2013.01); *G02B 6/34* (2013.01); *A61B 2018/00404* (2013.01); *A61B 2018/00595* (2013.01)

(58) Field of Classification Search
CPC .......... A61B 18/24; A61B 2018/00404; A61B 2018/00785; A61B 2018/00595;
(Continued)

(56) References Cited

U.S. PATENT DOCUMENTS

2004/0016581 A1   8/2004  Fujita
2007/0237449 A1*  10/2007  Aoki ................... G02B 6/4292
                                                       385/14
(Continued)

FOREIGN PATENT DOCUMENTS

EP    2 050 411 A1    4/2009
JP    61-257638 A     11/1986
(Continued)

OTHER PUBLICATIONS

Notice of Reasons for Refusal dated Jan. 18, 2022 in Japanese Patent Application No. 2020-546013 (with English machine translation), 5 pages.
(Continued)

*Primary Examiner* — Gary Jackson
*Assistant Examiner* — Sebastian X Lukjan
(74) *Attorney, Agent, or Firm* — Oblon, McClelland, Maier & Neustadt, L.L.P.

(57) ABSTRACT

An optical probe includes: an optical fiber; a reflecting portion; and a traveling direction changing portion changing a traveling direction of a laser beam of a first wavelength that has transmitted through the reflecting portion to a direction different from a traveling direction before transmitting through the reflecting portion. Further, the traveling direction changing portion is configured by a bending structure having a structure in which a portion on a distal end side of the optical fiber is bent, and the reflecting portion is provided closer to a proximal end side of the optical fiber than the bending structure.

18 Claims, 10 Drawing Sheets

(58) Field of Classification Search
CPC .... A61B 2018/2233; A61B 2018/2247; G02B 6/34; G02B 6/29317; G01M 11/00
See application file for complete search history.

(56) References Cited

U.S. PATENT DOCUMENTS

| | | |
|---|---|---|
| 2008/0285909 A1 | 11/2008 | Younge et al. |
| 2009/0317035 A1 | 12/2009 | Aoki et al. |
| 2010/0185187 A1* | 7/2010 | Yamashita ............ A61B 18/24 606/14 |
| 2016/0089203 A1* | 3/2016 | Shimizu ................ A61B 18/22 606/15 |
| 2018/0168729 A1 | 6/2018 | Pratten et al. |

FOREIGN PATENT DOCUMENTS

| | | |
|---|---|---|
| JP | 5-103774 A | 4/1993 |
| JP | 2007-264033 A | 10/2007 |
| JP | 2011-528581 A | 11/2011 |
| JP | 2012-154843 A | 8/2012 |
| JP | 2015-73704 A | 4/2015 |
| WO | WO 2013/114376 A1 | 8/2013 |

OTHER PUBLICATIONS

International Search Report dated Oct. 15, 2019 in PCT/JP2019/035404 filed Sep. 9, 2019, 1 page.
Extended European Search Report dated Apr. 21, 2022 in European Patent Application No. 19858840.2, 8 pages.

* cited by examiner

OPTICAL PROBE, MEDICAL LASER PROBE, AND CAUTERIZATION DEVICE

CROSS-REFERENCE TO RELATED APPLICATION(S)

This application is a continuation of International Application No. PCT/JP2019/035404, filed on Sep. 9, 2019 which claims the benefit of priority of the prior Japanese Patent Application No. 2018-168431, filed on Sep. 10, 2018, the entire contents of which are incorporated herein by reference.

BACKGROUND

The present disclosure relates to an optical probe, a medical laser probe, and a cauterization device.

BACKGROUND

Japanese Laid-open Patent Publication No. 2015-073704 discloses an optical probe in which an optical fiber for propagating a cauterizing laser beam is inserted inside an insertion member (catheter) inserted into a blood vessel of a living body for a laser device used as a medical device. Such an optical probe has a bending structure in which a distal end side portion of the optical fiber is curved into a hook shape with the catheter inserted in the blood vessel. Therefore, in such a medical device, a blood vessel wall located lateral to the insertion direction of the catheter can be cauterized by emitting a laser beam from a distal end surface of the optical fiber with the catheter inserted into the blood vessel.

Citation List

By the way, the laser device for irradiating the laser beam is not limited to the case where it is applied to a medical cauterization device, and may also be applied to an industrial laser processing device. The industrial laser processing device is also configured to emit a laser beam from the distal end surface of the optical fiber with the optical probe inserted inside a thin tube like a medical blood vessel. Then, in the laser device or the cauterization device using the optical fiber as described above, it is necessary to emit the laser beam with a desired intensity from the distal end surface of the optical fiber in order to perform desired laser processing or medically appropriate treatment (cauterization). If the fiber breaks in the middle, light leaks at a broken point, which causes problems such as not being able to obtain the desired intensity and damaging a healthy portion with the leaked light. In order to prevent the problems, it is desired to have a configuration capable of detecting the breakage of the optical fiber.

SUMMARY

There is a need for providing an optical probe, a medical laser probe, and a cauterization device that can irradiate a laser beam toward an irradiation target located lateral to an insertion direction, such as in a small-diameter tube, and can be applied to detect breakage of an optical fiber.

According to an embodiment, an optical probe includes: an optical fiber that propagates light of a plurality of wavelengths introduced from a plurality of light sources; a reflecting portion that is provided on the optical fiber, transmits a laser beam of a first wavelength of the plurality of wavelengths and reflects light of a second wavelength of the plurality of wavelengths; and a traveling direction changing portion that is provided on a distal end side of the optical fiber and changes a traveling direction of the laser beam of the first wavelength that has transmitted through the reflecting portion to a direction different from a traveling direction before transmitting through the reflecting portion. Further, the traveling direction changing portion is configured by a bending structure having a structure in which a portion on the distal end side of the optical fiber is bent, and the reflecting portion is provided closer to a proximal end side of the optical fiber than the bending structure.

DETAILED DESCRIPTION

In the configuration described in Japanese Laid-open Patent Publication No. 2015-073704, it is not possible to confirm the breakage of the optical fiber having a bending structure even if the optical fiber is broken in the middle.

Hereinafter, embodiments of the present disclosure will be described in detail with reference to the accompanying drawings. Note that the present disclosure is not limited to the embodiments described below. In addition, in the

First Embodiment

Figure 1:
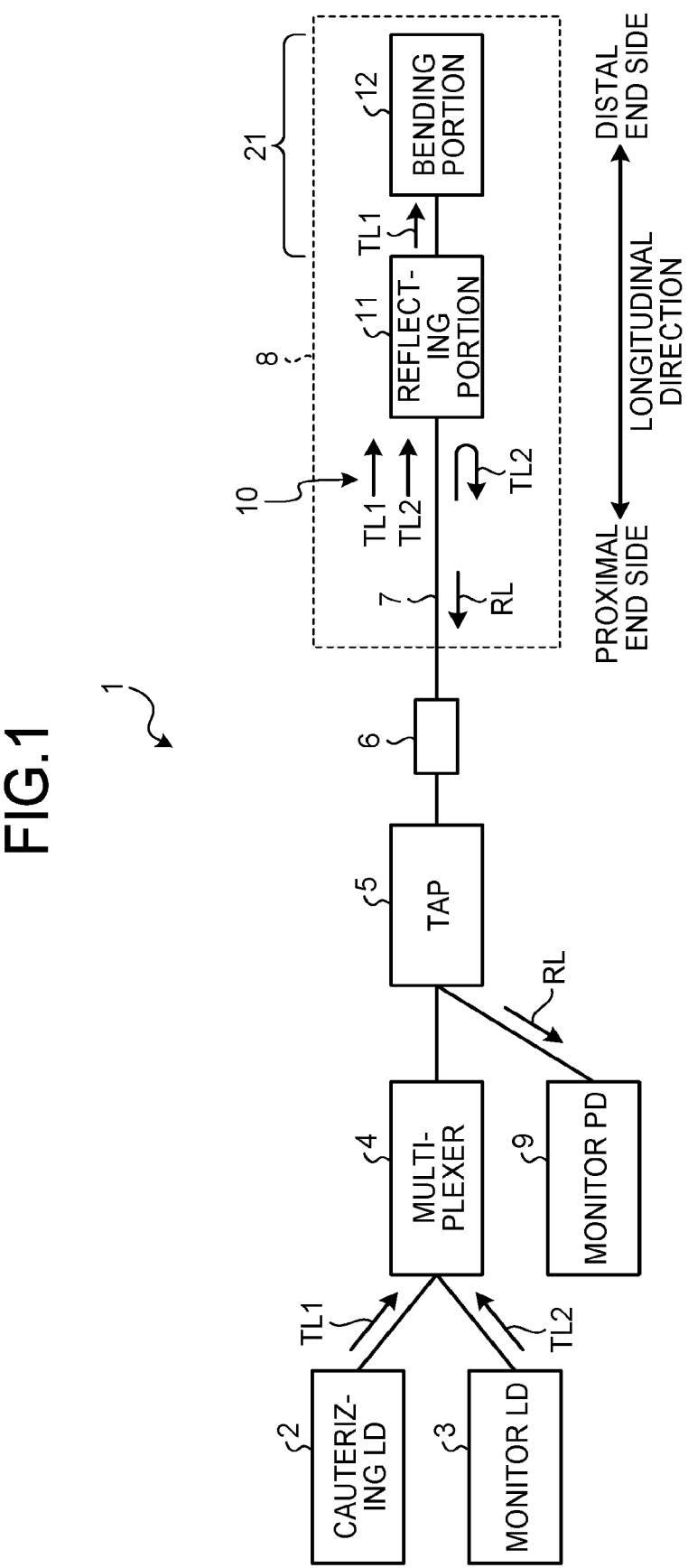
FIG. 1 is a configuration diagram schematically illustrating a laser device according to a first embodiment.

FIG. 1 is a configuration diagram schematically illustrating a laser device according to a first embodiment. A laser device 1 according to the first embodiment is a device that is configured to be usable as a medical laser cauterization device, and that propagates light of a plurality of wavelengths including a laser beam as cauterizing light through the same optical fiber.

Such a laser device 1 is configured such that the light of the plurality of wavelengths is propagated through the same optical fiber, monitor light (monitor light TL2) is reflected by a reflecting portion 11, and a cauterizing laser beam (cauterizing light TL1) passes through the reflecting portion 11 and is emitted by bending a traveling direction of the light at a bending portion 12 of the distal end side.

As illustrated in FIG. 1, the laser device 1 includes a cauterizing LD2, which is a first light source and a monitor LD3, which is a second light source. Note that the LD is a laser diode.

The cauterizing LD2 is a light source that outputs the cauterizing light TL1. The cauterizing light TL1 is light in a wavelength bandwidth called a so-called "living window", that is, light in a wavelength bandwidth from red to near infrared in the vicinity of 650 nm to 1400 nm. For the cauterizing light TL1, light of a wavelength of 980 nm is preferably used. In addition, the cauterizing LD2 has an output of 0.1 W or more. For the cauterizing LD2, an output of 1 W or more is preferably used.

The monitor LD3 is a light source that outputs the monitor light TL2. The monitor light TL2 is a monitor light for detecting breakage. The monitor light TL2 has a wavelength in the range including a visible light wavelength bandwidth to a near infrared wavelength bandwidth, and has a wavelength of 1600 µm or less. Specifically, the monitor light TL2 has 400 nm to 800 nm, and preferably has a short wavelength of 600 nm to 650 nm as an optimum solution. Preferably, monitor light of a wavelength of 635 nm or a wavelength of 650 nm included in the visible light wavelength bandwidth is used. Since the influence of bending loss is small, it is preferable that the monitor light TL2 has a short wavelength. On the other hand, since there is concern about durability of the optical fiber if the wavelength is shorter than 400 nm, the monitor light TL2 is preferably 400 nm or more.

In addition, the monitor LD3 has an output of 5 mW or less. For the monitor LD3, a device (at a connection portion 6) having an output of 1 mW or less is preferably used. That is, the power of the monitor light TL2 is 5 mW or less, preferably 1 mW or less. As a result, the monitor light TL2 is designed with eye safety in mind. In addition, the monitor LD3 may be configured to output a plurality of different wavelengths. For example, as the monitor LD3, LDs that output light of a plurality of different wavelengths may be collectively used as the monitor LD3. The outputs of the plurality of LDs may be multiplexed (combined) in advance with a multiplexer (not illustrated), or the outputs of the plurality of LDs may be directly input to a multiplexer 4.

The cauterizing LD2 and the monitor LD3 are connected to an input side of the multiplexer 4. The multiplexer 4 multiplexes (combines) the cauterizing light TL1 output from the cauterizing LD2 and the monitor light TL2 output from the monitor LD3. The multiplexer 4 is configured by, for example, a wavelength division multiplexing (WDM) coupler, an optical combiner, a tap coupler, a space-coupled optical system, and the like. In addition, although not illustrated in FIG. 1, a plurality of multiplexers 4 may be connected. For example, as the plurality of multiplexers 4, two optical combiners can be stacked in two stages and used in 2 by 1 or 3 by 1. Alternatively, as the plurality of multiplexers 4, a combination of the optical combiner and the tap coupler can be used. In this case, a combination ratio of the tap coupler is preferably a ratio of 80:20 or more, and for example, 90:10, 95:5, and 99:1 can be set.

A tap coupler (TAP) 5 that functions as an extraction portion for monitoring reflected light RL is connected to an output side of the multiplexer 4. The output from the multiplexer 4 is input to an input portion of the tap coupler 5. An optical fiber 7 is optically connected to an output portion of the tap coupler 5 via the connection portion 6. Such a tap coupler 5 has a configuration necessary for monitoring the reflected light RL, and functions as a tap coupler (a tap coupler for receiving monitor light) for extracting the reflected light RL. For example, the tap coupler 5 is an asymmetric tap coupler, and the combination ratio can be set to 80:20 or more, preferably 90:10, 95:5, and 99:1. More preferably, the tap coupler 5 is set to a combination ratio of 99:1.

The connection portion 6 is configured to make the optical probe 10 replaceable. The connection portion 6 is provided between the tap coupler 5 and the optical fiber 7. The optical probe 10 has a configuration including the optical fiber 7 closer to the distal end side than the connection portion 6, and includes a reflecting portion 11 and a bending portion 12 provided on the optical fiber 7.

When the laser device 1 is a medical laser cauterization device, the optical probe 10 is inserted inside a catheter 8 and inserted inside a blood vessel.

The optical probe 10 and the catheter 8 constitute a medical laser probe. Such a catheter 8 is a disposable part. The optical probe 10 is also a disposable part. Therefore, since the optical probe 10 and the catheter 8 are disposable, the connection portion 6 is provided so that the optical fiber 7 can be attached to and detached from the tap coupler 5. That is, the connection portion 6 connects the catheter 8 on a disposable side and the device on a reuse side. For example, in the connection portion 6, in addition to the connectors used for normal fiber connection (FC connector, SC connector, SMA connector, ST connector, etc.), the device and the optical fiber 7 may be connected by spatial coupling by a lens. That is, the connection portion 6 is configured by a connector having a connection end surface (connector end surface) and a spatial coupling portion having a lens. When the connection portion 6 is configured by the connector, there is a risk of ignition by the laser beam if fine foreign matter has entered the connection end surface, but when the connection portion 6 is configured by the spatial coupling, this can be suppressed. In addition, the connection portion 6 is configured to be detachable from the optical fiber 7 in addition to the tap coupler 5. As a result, in the optical probe 10, the connection portion 6 can be removed from the optical fiber 7 and replaced.

The power of the laser beam passing through the connection portion 6 is 100 W or less. Preferably, the power of the laser beam passing through the connection portion 6 is 1 W to 30 W. That is, the power of the cauterizing light TL1 passing through the connection portion 6 is 100 W or less, preferably 1 W to 30 W. As a result, when the connection portion 6 is configured by the spatial coupling portion, deterioration and ignition at the spatial coupling portion can be suppressed. Further, with respect to the connection portion 6, an optimum wavelength of the spatial coupling portion is set to be substantially equal to the wavelength of the cauterizing light TL1. As a result, the leakage of the laser beam to the outside can be minimized, and the reliability of the connection portion 6 can be improved.

The optical fiber 7 is an optical fiber that propagates the cauterizing light TL1 output from the cauterizing LD2 and the monitor light TL2 output from the monitor LD3, and extends in a longitudinal direction. The optical fiber 7 is provided with the reflecting portion 11 having a reflecting function and the bending portion 12 having a function of changing the traveling direction of light (traveling direction changing function). The reflecting function is a function of reflecting a portion of the light propagating in the optical fiber 7 toward a proximal end side in the longitudinal direction. The function of changing the traveling direction of light is a function of changing the traveling direction of light transmitted through the reflecting portion 11 in a direction different from the traveling direction before transmitting through the reflecting portion 11.

The reflecting portion 11 transmits the cauterizing light TL1 and reflects the monitor light TL2. That is, the reflecting portion 11 is configured by a member that reflects light of at least one wavelength and transmits at least one wavelength. For example, the reflecting portion 11 is configured by a fiber Bragg grating (FBG) or a reflective film. A reflectivity of the reflecting portion 11 is larger than the Fresnel reflectivity. For example, when it is used for detecting the breakage of the optical fiber 7, the reflectivity of the reflecting portion 11 is 40% or more. In this way, by providing the reflecting portion 11 at a portion on the distal end side of the optical fiber 7, it is possible to monitor a light transmission state.

The bending portion 12 is provided at a portion on the distal end side of the optical fiber 7. The bending portion 12 changes the traveling direction of the cauterizing light TL1 transmitted through the reflecting portion 11 to a direction different from the traveling direction before transmitting through the reflecting portion 11 at a position closer to the distal end side than the reflecting portion 11. That is, in the first embodiment, the bending portion 12 is provided as a traveling direction changing portion that changes the traveling direction of the cauterizing light TL1 transmitted through the reflecting portion 11 to a direction different from the traveling direction before transmitting through the reflecting portion 11.

Figure 2:
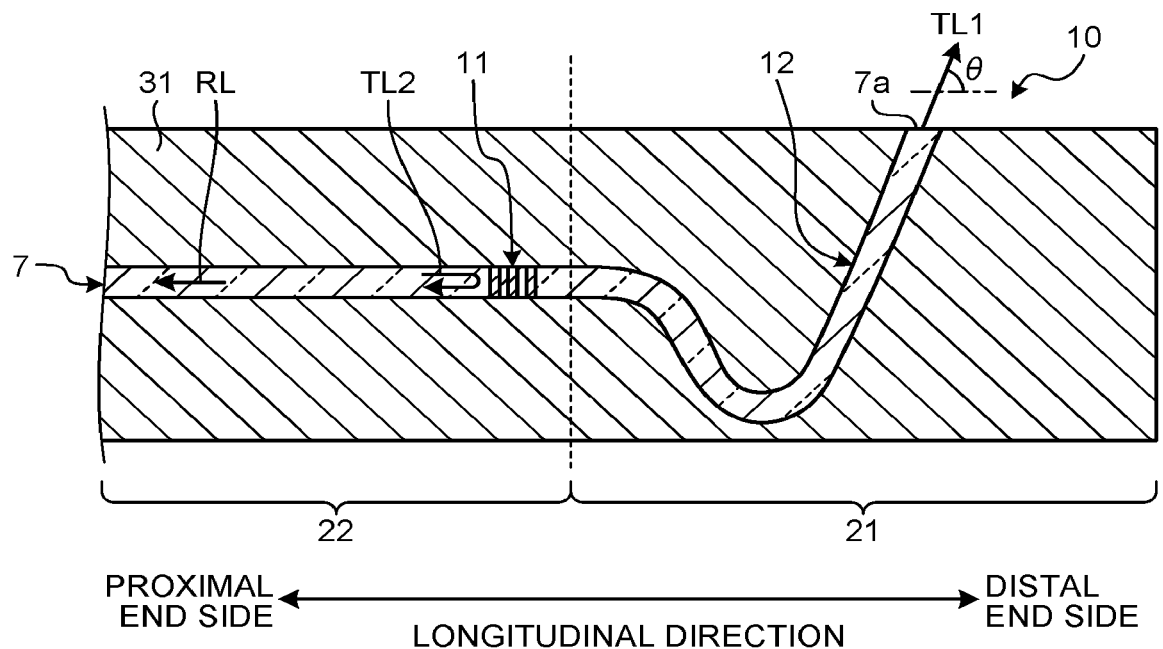
FIG. 2 is a cross-sectional view for explaining a portion on a distal end side of an optical fiber.

For example, as illustrated in FIG. 2, the bending portion 12 is configured by a bending structure having a structure in which the portion of the distal end side of the optical fiber 7 is curved. In the optical probe 10, the reflecting portion 11 made of an FBG is provided on the proximal end side as compared to the bending structure. The reflecting portion 11 made of an FBG is formed in the optical fiber 7. The optical fiber 7 includes a core, a clad, and a fiber coating formed on an outer circumferential portion of the clad. The core and the clad of the optical fiber 7 are made of a known constituent material such as glass. Then, the optical fiber 7 emits the cauterizing light TL1 from a distal end surface 7*a* provided on the distal end side as compared to the bending portion 12 having the bending structure.

In addition, the monitor light TL2 reflected by the reflecting portion 11 propagates as reflected light RL so as to return toward the proximal end side of the optical fiber 7, and is input to a monitor PD9 from the proximal end side of the optical fiber 7 via the connection portion 6 and the tap coupler 5.

The monitor PD9 is a light receiving portion for monitoring the light reflected by the reflecting portion 11. The PD is a photodiode. A monitor portion including the monitor PD9 enables a monitor based on the reflected monitor light TL2. For example, when the reflecting portion 11 is configured by the FBG, it is usually possible to monitor things such as temperature that can be monitored by the FBG. In addition, a plurality of monitor PD9s may be installed, and may be configured to monitor light of different wavelengths output from the monitor LD3. For example, between the monitor PD9 and the tap coupler 5, the WDM coupler is inserted to demultiplex the light, or a tap coupler is inserted to demultiplex the light, and light of a specific wavelength is configured to be input to the monitor PD9 by inserting a bandpass filter after demultiplexing.

As illustrated in FIG. 2, in the optical probe 10 in which the reflecting portion 11 is configured by the FBG, the reflecting portion 11 is provided at the proximal end side as compared to the bending portion 12. The bending portion 12 is provided at a distal end portion 21 of the optical probe 10, and a reflecting portion 11 is provided at an intermediate portion 22 of the optical probe 10. The intermediate portion 22 is located closer to the proximal end side than the distal end portion 21. Since the bending portion 12 is configured by the bending structure in which the portion of the distal end side of the optical fiber 7 has a curved shape, the FBG is formed on the optical fiber 7 closer to the proximal end side than the bending portion 12 in order to prevent the monitor light TL2 from being affected by a bending loss due to the bending portion 12. The reflecting portion 11 made of the FBG reflects the monitor light TL2 toward the proximal end side and transmits the cauterizing light TL1 toward the distal end side.

In addition, the bending portion 12 having the bending structure is held in a curved shape by a protective material 31 of the optical fiber 7. In particular, in the shape of the bending portion 12 illustrated in FIG. 2, a portion of the distal end side as compared to reflecting portion 11 is curved in one direction in the direction intersecting the longitudinal direction, and then curved again in the other direction. Then, the distal end surface 7*a* of the optical fiber 7 is formed so that the cauterizing light TL1 can be irradiated in a direction inclined at a predetermined inclination angle θ with respect to an extending direction of the optical probe 10. The inclination angle θ is preferably in the range of 10 degrees to 170 degrees. By setting such an inclination angle θ, when the catheter 8 is inserted into the blood vessel, the cauterizing light TL1 can be suitably emitted from the distal end surface 7*a* toward the blood vessel wall. The protective material 31 is configured by a material such as resin, plastic, or ceramic.

As described above, according to the first embodiment, it is possible to detect the breakage of the optical fiber 7 for the optical probe 10 inserted into the catheter 8 inserted into the blood vessel as the medical cauterization device, and emit the cauterizing light TL1 toward the blood vessel wall located lateral to the insertion direction.

The optical probe 10 of the first embodiment has the bending structure at the distal end side of the optical fiber 7 in order to emit the cauterizing light TL1 toward an irradiation target located lateral to the insertion direction of the catheter 8, and reflects the monitor light TL2 toward the proximal end side by the reflecting portion 11. As a result, the breakage detection of the optical fiber 7 becomes possible by monitoring the reflected light RL reflected by the reflecting portion 11. Further, by providing the reflecting portion 11 on the proximal end side as compared to the bending portion 12, the bending loss of the reflected light RL can be reduced, and the breakage of the optical fiber 7 can be appropriately detected.

As described above, in the laser device 1 of the first embodiment, since the bending loss of the monitor light TL2 is small, it can be determined that all the decrease in the intensity of the reflected light RL is due to the breakage of the optical fiber 7 in a state where the connection portion 6 is normally connected. As a result, even when it is difficult to detect whether or not the optical fiber 7 is broken, such as a crack in the optical fiber 7, it can be detected by the monitor of the reflected light RL. Further, for the laser device 1 provided with the connection portion 6, it is possible to detect an abnormal dropout at the connection portion 6 by monitoring the reflected light RL. In this case, as an abnormality of the connection portion 6, an abnormality of the connector end surface such as dirt on the connector end surface can be detected.

MODIFIED EXAMPLES OF FIRST EMBODIMENT

Here, modified examples of the first embodiment will be described with reference to FIGS. 3 to 6. Note that FIGS. 3 to 6 schematically illustrate the configuration of the optical probe 10 in each modified example.

Figure 3:
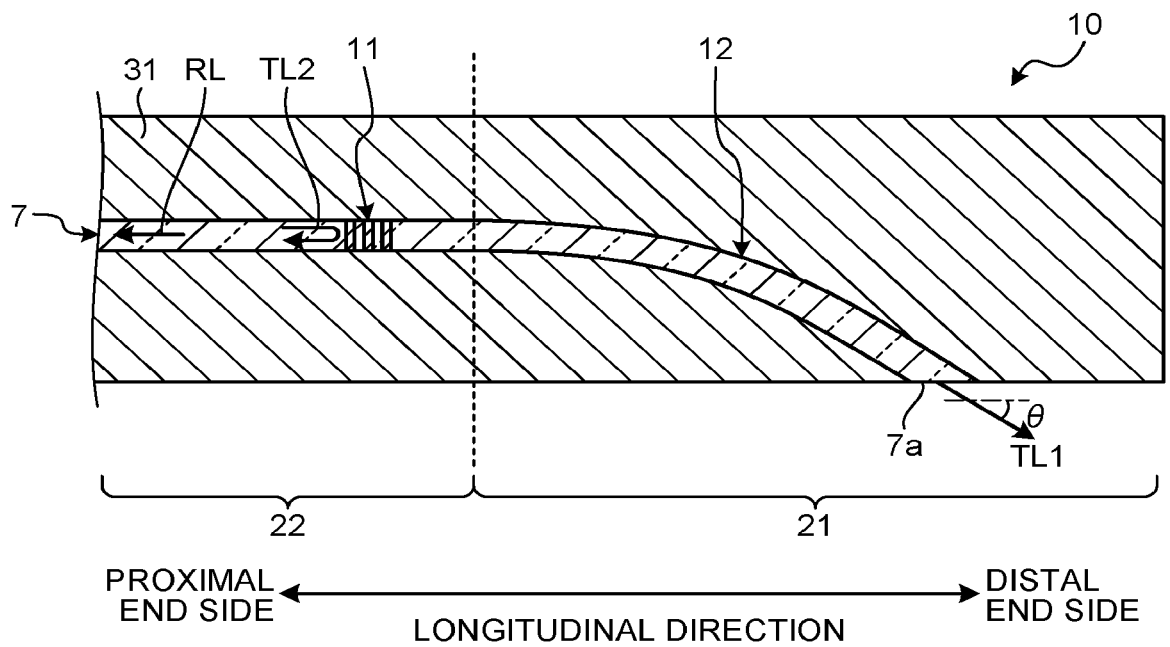
FIG. 3 is a cross-sectional view for explaining a modified example 1 of the first embodiment.

FIG. 3 is a cross-sectional view for explaining a modified example 1 of the first embodiment. As illustrated in FIG. 3, in the modified example 1 of the first embodiment, the bending structure of the bending portion 12 continues to bend in one direction in a direction intersecting the longitudinal direction. The reflecting portion 11 is configured by an FBG. The optical fiber 7 is configured to have a shape in which a portion of the distal end side as compared to the reflecting portion 11 continues to bend in one direction in the direction intersecting the longitudinal direction to reach the distal end surface 7a. As described above, when the bending portion 12 is formed by the bending structure of the optical fiber 7, the bending structure is not limited to the shape illustrated in FIG. 2 described above. That is, even when the optical fiber 7 has the bending portion 12 configured by the bending structure, the bending method is not particularly limited as long as the cauterizing light TL1 emitted from the distal end surface 7a of the optical fiber 7 via the bending portion 12 has a bending structure that can secure a desired intensity.

According to the modified example 1 configured in this way, when forming the reflective film as the reflecting portion 11 in the intermediate portion 22 and then forming the bending structure (bending portion 12) for changing the direction of propagation of light to a predetermined direction for the distal end portion 21 on the distal end side thereof, it is possible to monitor the presence or absence of damage caused during the process. This makes it possible to distinguish between a normal optical probe 10 and an optical probe that is damaged during the formation of the bending structure.

Figure 4:
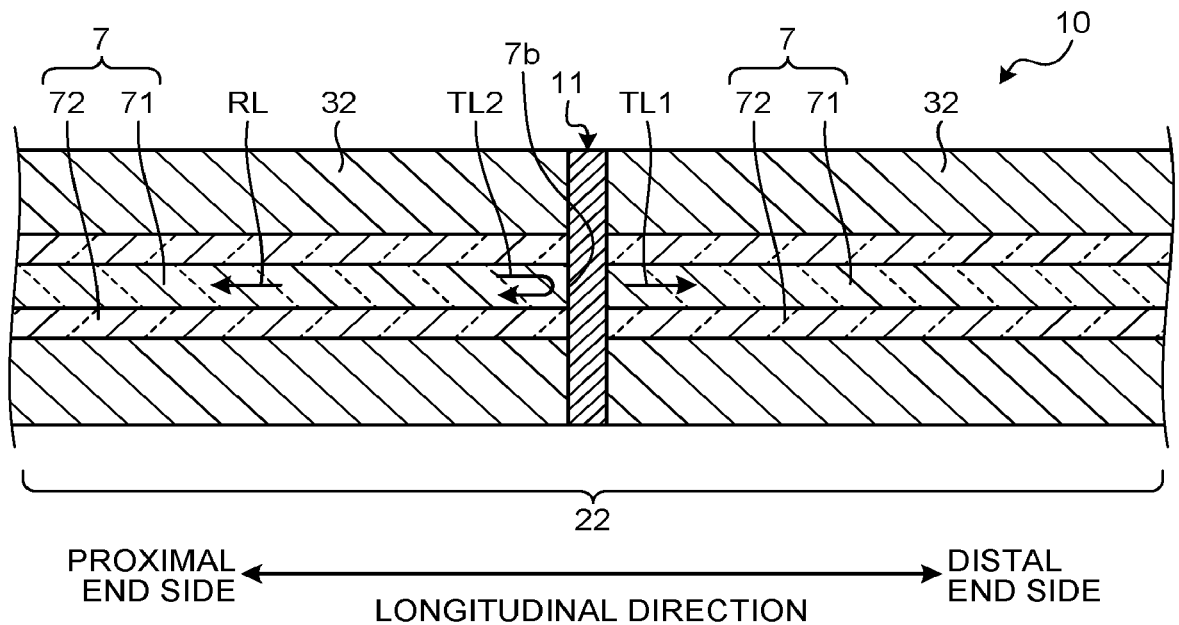
FIG. 4 is a cross-sectional view for explaining a modified example 2 of the first embodiment.

FIG. 4 is a cross-sectional view for explaining a modified example 2 of the first embodiment. As illustrated in FIG. 4, in the modified example 2 of the first embodiment, the reflecting portion 11 is configured by a reflective film. A slit 7b is formed in the intermediate portion 22 of the optical probe 10 along a surface orthogonal to the longitudinal direction of the optical fiber 7. The slit 7b is formed in a core 71 and a clad 72 of the optical fiber 7. A reflective film is provided as the reflecting portion 11 in the slit 7b. The reflective film as the reflecting portion 11 is configured by a metal film, a dielectric multilayer film or the like. In addition, in the example illustrated in FIG. 4, the reflective film in the slit 7b is fixed to the optical fiber 7 by a fiber coating 32. As described above, in the optical probe 10 provided with the slit 7b and the reflecting portion 11 configured by the reflective film in the intermediate portion 22, it is possible to provide the bending portion 12 having the above-mentioned bending structure at the distal end portion 21 thereof.

Figure 5:
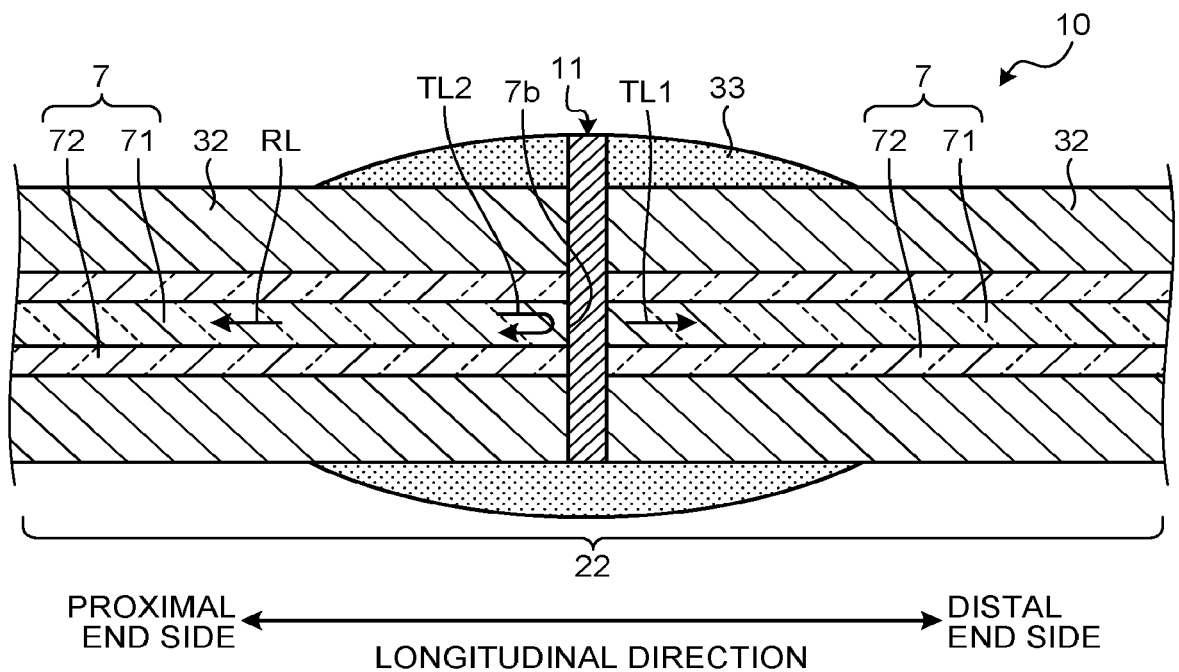
FIG. 5 is a cross-sectional view for explaining a modified example 3 of the first embodiment.

FIG. 5 is a cross-sectional view for explaining a modified example 3 of the first embodiment. As illustrated in FIG. 5, in the modified example 3 of the first embodiment, in the intermediate portion 22 of the optical probe 10, the reflecting portion 11 configured by the reflective film is formed to be larger than the fiber coating 32. The reflective film is fixed to the optical probe 10 by a protective material 33. The protective material 33 is provided so as to cover a portion of the outer circumferential portion of the fiber coating 32. In this way, when the reflective film is provided in the intermediate portion 22 of the optical probe 10, the protective material 33 may protect the formed portion of the reflecting portion 11. The protective material 33 is configured by a material such as resin, plastic, or ceramic.

Figure 6:
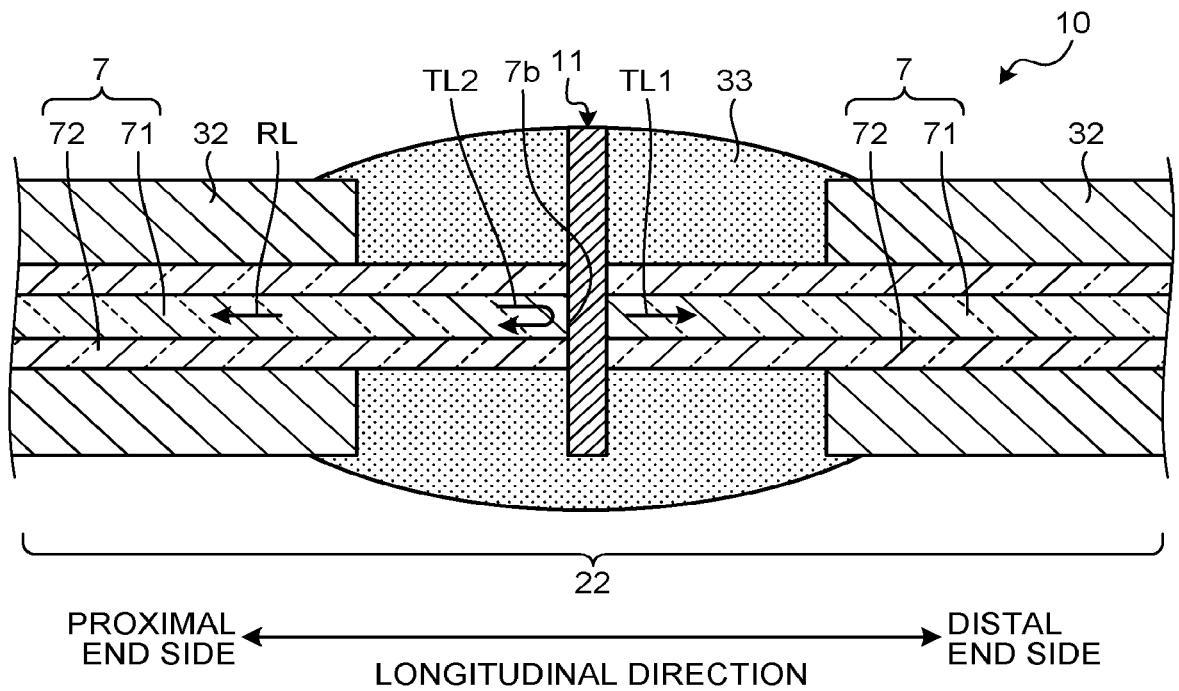
FIG. 6 is a cross-sectional view for explaining a modified example 4 of the first embodiment.

FIG. 6 is a cross-sectional view for explaining a modified example 4 of the first embodiment. As illustrated in FIG. 6, in the modified example 4 of the first embodiment, the fiber coating 32 is divided at the intermediate portion 22 of the optical probe 10. A protective material 33 for the optical fiber 7 is provided at a portion where the fiber coating 32 is divided, and the slit 7b for providing the reflective film is formed in the optical fiber 7. The reflective film provided in the slit 7b is fixed to the optical fiber 7 by the protective material 33. The protective material 33 is provided so as to cover the outer circumferential portion of the clad 72 of the optical fiber 7. In this way, even in the intermediate portion 22 of the optical probe 10, the reflective film can be formed with a portion of the fiber coating 32 peeled off. Then, the portion where the fiber coating 32 is peeled off can be protected by the protective material 33.

Second Embodiment

Next, the optical probe 10 according to a second embodiment will be described. In the second embodiment, the configurations of the reflecting portion 11 and the bending portion 12 included in the optical probe 10 are different from those of the first embodiment. The configurations of the laser device 1 other than the optical probe 10, for example, the configurations closer to the proximal end side than the connection portion 6, are the same as those of the first embodiment in the second embodiment. In the description of the second embodiment, the description of the same configuration as that of the first embodiment will be omitted, and the reference numerals thereof will be cited.

Figure 7:
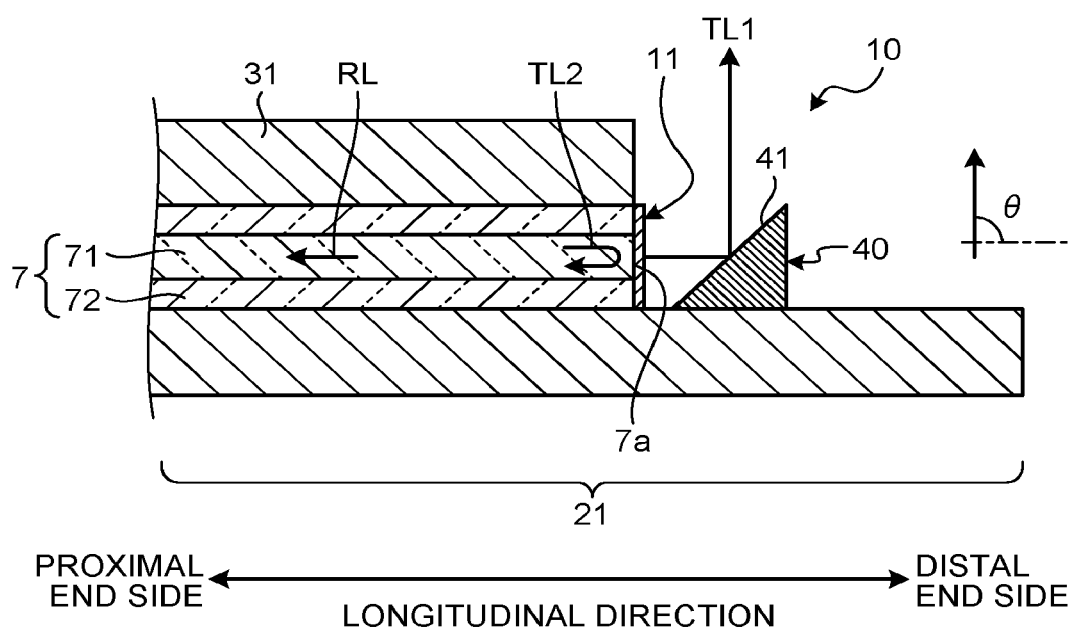
FIG. 7 is a cross-sectional view for explaining a portion on a distal end side of an optical fiber included in a laser device according to a second embodiment.

FIG. 7 is a cross-sectional view for explaining the optical probe 10 according to the second embodiment. As illustrated in FIG. 7, in the optical probe 10 of the second embodiment, the reflecting portion 11 is provided on the distal end surface 7a of the optical fiber 7. The reflecting portion 11 is configured by a reflective film. In the second embodiment, a side surface irradiation mechanism 40 is provided as a traveling direction changing portion that changes the traveling direction of the cauterizing light TL1 transmitted through the reflecting portion 11 to a direction different from the traveling direction before transmitting through the reflecting portion 11.

The side surface irradiation mechanism 40 has a reflecting surface 41 arranged in front (distal end side) of the distal end surface 7a with respect to the reflecting portion 11 configured by the reflective film. The reflecting surface 41 is formed so as to be inclined by a predetermined inclination angle θ with respect to the extending direction of the optical fiber 7. As a result, the cauterizing light TL1 emitted from the distal end surface 7a and transmitted through the reflecting portion 11 configured by the reflective film is irradiated by the side surface irradiation mechanism 40 toward the side in the longitudinal direction. In addition, the reflecting portion 11 as the reflective film is provided on the distal end surface 7a by a known vapor deposition or chemical vapor deposition (CVD) method or the like. Note that the reflective film may be separately manufactured and provided by being attached to the distal end surface 7a with an adhesive, a gluing agent or the like.

In the second embodiment, the optical fiber 7 included in the optical probe 10 extends in a linear shape, and the reflective film is provided on the distal end surface 7a thereof. The monitor light TL2 reflected by the reflecting portion 11 configured by the reflective film propagates as reflected light RL so as to return toward the proximal end side of the optical probe 10.

As described above, according to the second embodiment, since the side surface irradiation mechanism 40 is provided on the distal end portion 21 of the optical probe 10, the cauterizing light TL1 can be irradiated laterally with respect to the extending direction of the optical fiber 7. In addition, since the reflecting portion 11 configured by the reflective film is integrally formed on the distal end surface 7a of the optical fiber 7, the return light (reflected light RL) of the monitor light TL2 reflected by the reflective film can be monitored. Further, since the reflecting portion 11 configured by the reflective film is integrally formed on the distal end surface 7a of the optical fiber 7, the structure is simpler and smaller than the structure in which the distal end surface 7a and the reflective member are arranged apart from each other. Further, since the optical fiber 7 constituting the optical probe 10 does not have the bending structure, a diameter of the optical probe 10 can be reduced and a diameter of the catheter 8 can be reduced.

MODIFIED EXAMPLES OF SECOND EMBODIMENT

Here, modified examples of the second embodiment will be described with reference to FIGS. 8 to 10. Note that FIGS. 8 to 10 schematically illustrate the configuration of the optical probe 10 in each modified example.

Figure 8:
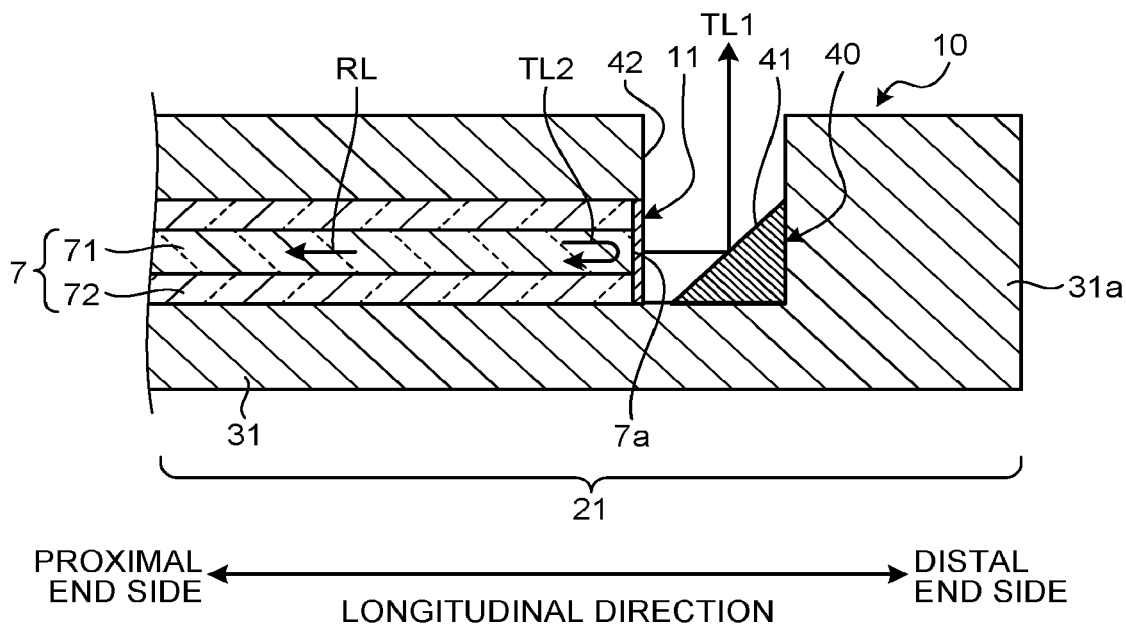
FIG. 8 is a cross-sectional view for explaining a modified example 1 of the second embodiment.

FIG. 8 is a cross-sectional view for explaining a modified example 1 of the second embodiment. As illustrated in FIG. 8, the side surface irradiation mechanism 40 is fixed to the protective material 31 by a holding portion 31a provided on the distal end side thereof. The holding portion 31a is configured by a portion of the protective material 31. In addition, an emitting window 42 is formed by the protective material 31 having the holding portion 31a. The emitting window 42 forms a portion through which the cauterizing light TL1 reflected by the reflecting surface 41 of the side surface irradiation mechanism 40 passes.

Figure 9:
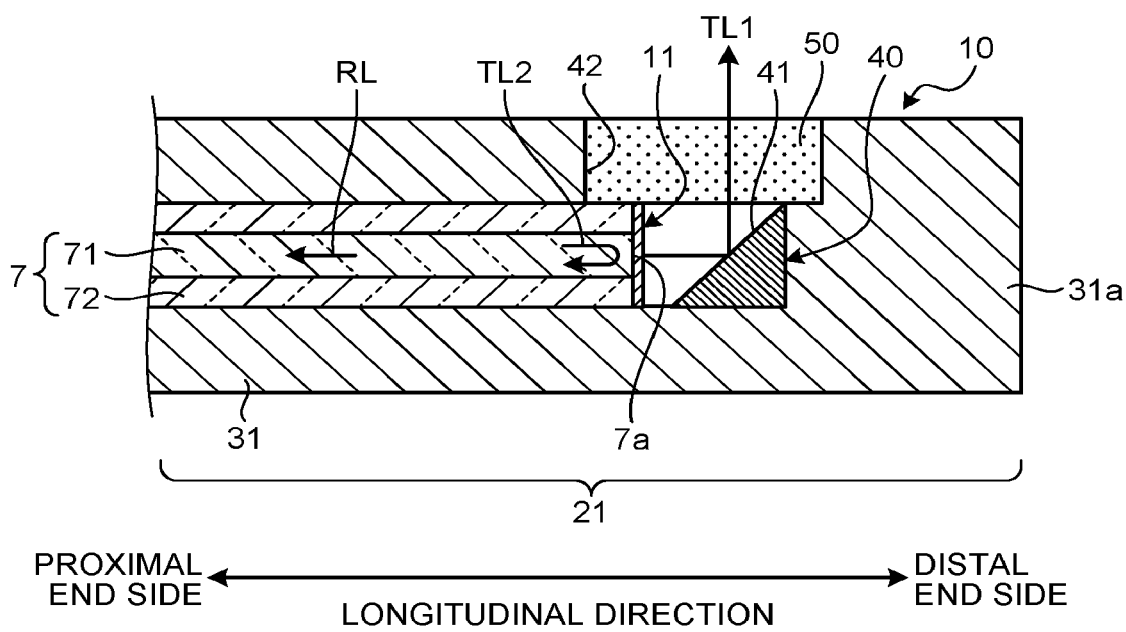
FIG. 9 is a cross-sectional view for explaining a modified example 2 of the second embodiment.

FIG. 9 is a cross-sectional view for explaining a modified example 2 of the second embodiment. As illustrated in FIG. 9, the emitting window 42 formed by the holding portion 31a is provided with a light transmitting member 50 that transmits the cauterizing light TL1. The side surface irradiation mechanism 40 is housed inside the optical probe 10 by the light transmitting member 50 and the protective material 31.

Figure 10:
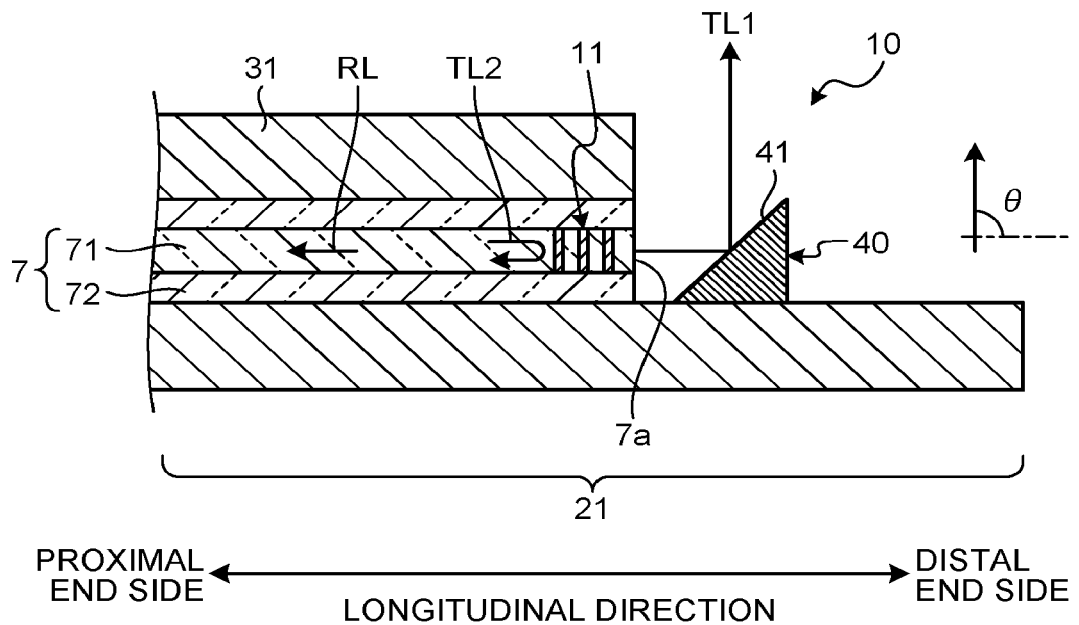
FIG. 10 is a cross-sectional view for explaining a modified example 3 of the second embodiment.

FIG. 10 is a cross-sectional view for explaining a modified example 3 of the second embodiment. As illustrated in FIG. 10, even in the configuration including the side surface irradiation mechanism 40, the reflecting portion 11 is configured by the FBG. In the modified example 3 illustrated in FIG. 10, regarding the configuration of the second embodiment illustrated in FIG. 7, the reflecting portion 11 configured by the reflective film is changed to the reflecting portion 11 configured by the FBG. That is, regarding the configuration of the modified example 1 illustrated in FIG. 8, the reflecting portion 11 configured by the reflective film can be changed to the reflecting portion 11 configured by the FBG illustrated in FIG. 10 to provide the modified example 3. Similarly, regarding the configuration of the modified example 2 illustrated in FIG. 9, the reflecting portion 11 configured by the reflective film may be changed to the reflecting portion 11 configured by the FBG illustrated in FIG. 10 to provide the modified example 3.

MODIFIED EXAMPLE OF EACH EMBODIMENT

Figure 11:
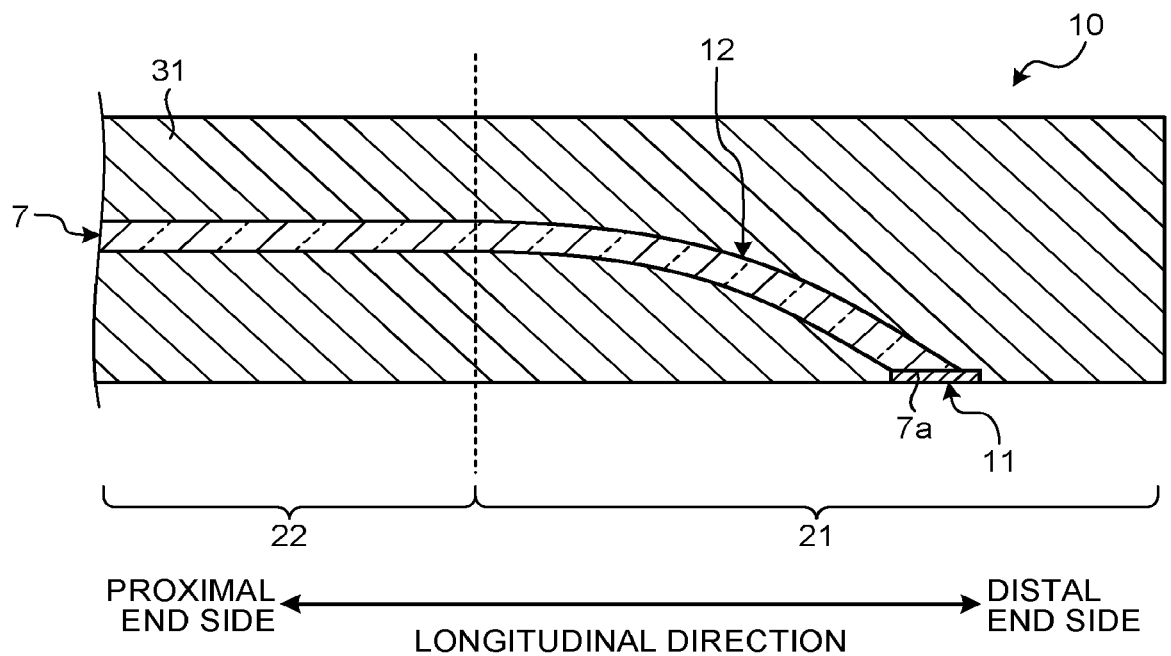
FIG. 11 is a cross-sectional view for explaining a modified example of each embodiment.

FIG. 11 is a cross-sectional view for explaining a modified example of each embodiment. As illustrated in FIG. 11, as the optical probe 10 of the modified example, the reflecting portion 11 configured by the reflective film may be integrally formed on the distal end surface 7a of the optical fiber 7, and the distal end side portion of the optical fiber 7 may be configured to have the bending portion 12 configured by a curved bending structure.

In addition, among the above-described embodiments and modified examples, except for the configuration in which the reflecting portion 11 configured by the reflective film is provided on the distal end surface 7a, the distal end of the optical fiber 7 may be configured to have a conical shape, and the optical fiber 7 may be configured to emit the cauterizing light TL1 as an annular beam. If it is an annular beam, it is possible to irradiate the cauterizing light TL1 toward a front side surface. That is, the distal end having the conical shape of the optical fiber 7 exerts the function of changing the traveling direction. As an example, the optical probe 10 included in the intermediate portion 22 illustrated in FIG. 4 may have the conical shape at the distal end of the optical fiber 7 instead of the bending structure.

In addition, in each of the above-described embodiments and modified examples, a bending amount of the optical fiber 7 can be estimated by using the monitor light TL3 output from the monitor LD3 and having a wavelength different from that of the monitor light TL2. The monitor LD3 outputs a monitor light for detecting breakage (monitor light TL2) and a monitor light for estimating the bending amount (monitor light TL3). That is, the power of the monitor light TL3 is 5 mW or less, preferably 1 mW or less. As a result, the monitor light TL3 is designed with eye safety in mind. At this time, the reflecting portion 11 is configured to reflect at least the monitor light TL2 and the monitor light TL3, and is configured to transmit the cauterizing light TL1. Further, the monitor light TL3 has 800 nm to 2000 nm, and preferably has a long wavelength of 1300 nm to 1600 nm as an optimum solution. As for the wavelength for bending detection, the longer wavelength is more sensitive to bending, and the detection sensitivity is increased.

In addition, preferably, the wavelength for detecting the breakage of the optical fiber 7 is shorter than the wavelength for estimating the bending amount of the optical fiber 7. Therefore, the wavelength of the monitor light TL2 is preferably shorter than the wavelength of the monitor light TL3.

The bending amount of the optical fiber 7 is estimated by the following procedure. First, the monitor PD9 measures the intensity of the monitor light TL3 before the optical probe 10 is inserted into the body, and then monitors an optical intensity of the monitor light TL3 when the optical probe 10 is inserted into the body. Every time the optical probe 10 bends in the body, since the loss due to the bending of the optical fiber 7 increases, the optical intensity of the monitor light TL3 decreases. By monitoring such a reduction rate with the monitor PD9, it is possible to estimate the bending amount of the optical fiber 7. In general, since the loss due to bending of the optical fiber 7 increases as the wavelength becomes longer, the optical intensity of the monitor light TL2 does not change as compared with the optical intensity of the monitor light TL3. Therefore, the monitor light TL2 can detect the breakage of the optical fiber 7 without being affected by the loss due to the bending of the optical fiber 7.

When the reflecting portion 11 is configured to reflect at least the monitor light TL2 and the monitor light TL3, the reflecting portion 11 may be configured by a single reflective material or a plurality of reflective materials. For example, the reflecting portion 11 may be configured by the reflective film that reflects a single wide band, or may be configured to reflect a plurality of wavelengths by combining the FBG and the reflective film.

In addition, a reflectivity of the monitor light TL3 is a degree in which the amount of attenuation due to bending of the optical fiber 7 can be measured. Therefore, the reflectivity of the monitor light TL3 may be 1% or more, and the reflectivity of the monitor light TL3 may be about the same as the Fresnel reflectivity. That is, Fresnel reflection on a cross section on the distal end side of the optical fiber 7 may be used as the reflecting portion of the monitor light TL3.

In addition, the laser device 1 of the modified example may use two or more optical combiners to collect a plurality of cauterizing laser beams. The laser device 1 of such a modified example includes one or more cauterizing laser diodes (cauterizing LD2) and two or more optical combiners (multiplexer 4), and the optical combiners are connected in series (cascade connection). That is, an output side of the cauterizing LD2 may be connected to an input side of one optical combiner (first multiplexer 4), and an output side of the one optical combiner may be connected to an input side of another optical combiner (second multiplexer 4). In this case, the optical combiner constituting the multiplexer 4 is an N:1 optical combiner, preferably a 2:1 optical combiner. Such an optical combiner multiplexes (combines) a plurality of cauterizing light TL1s, and is an end-couple type or side-couple type combiner.

Further, when a plurality of cauterizing LD2s are provided as described above, the plurality of cauterizing LD2s may be connected to the input side of the one optical combiner (first multiplexer 4). Alternatively, one cauterizing laser diode (first cauterizing LD2) may be connected to the input side of the one optical combiner (first multiplexer 4), and another cauterizing laser diode (second cauterizing LD2) and the output side of the one optical combiner (output side of the first multiplexer 4) may be connected to the input side of the other optical combiner (second multiplexer 4).

MODIFIED EXAMPLE 1

In addition, as yet another modified example of each embodiment, the laser device 1 may include a beam profile converter. The beam profile converter is a device that converts a profile of a beam to be irradiated (emitted) into a profile different from a profile of a beam to be incident. For example, the laser device 1 can be configured to include the beam profile converter between the reflecting portion 11 and the bending portion 12 inside the catheter 8. Note that in this description, a laser cauterization device including the beam profile converter will be described as a modified example 1 of each embodiment.

Figure 12:
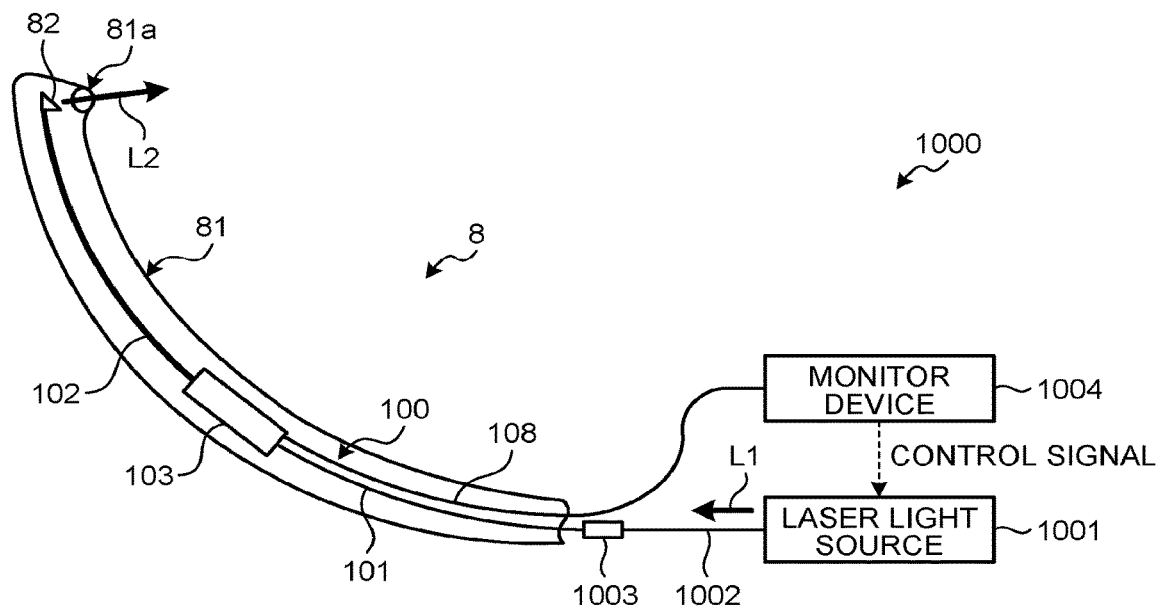
FIG. 12 is a schematic view illustrating a schematic configuration of a laser device according to a modified example 1 of each embodiment.

Here, a configuration example of the beam profile converter will be described with reference to FIGS. 12 to 14. FIG. 12 is a schematic view illustrating a schematic configuration of a laser device according to a modified example 1 of each embodiment. A laser device 1000 in the modified example 1 includes a laser light source 1001, an output optical fiber 1002, a connection portion 1003, a monitor device 1004, and a catheter 8. The catheter 8 includes a catheter body 81, an optical element 82, and a beam profile converter 100. The beam profile converter 100 includes at least an optical fiber 101, an optical fiber 102, and a housing 103.

The laser light source 1001 includes a laser light source such as an optical fiber laser, and outputs a cauterizing laser beam L1 (cauterizing light TL1) to the output optical fiber 1002. The output optical fiber 1002 is a single mode optical fiber or a multi-mode optical fiber. The output optical fiber 1002 is optically connected to the optical fiber 101 of the beam profile converter 100 via the connection portion 1003. As a result, the laser light source 1001 can output the laser beam L1 to the optical fiber 101. The connection portion 1003 may have the same configuration as the connection portion 6 described above.

In the catheter 8, the catheter body 81 is made of a flexible material such as resin. The catheter body 81 may have a laser beam output window 81a made of a material having excellent laser beam transmission. Note that for the sake of explanation, FIG. 12 illustrates the catheter body 81 transparently. A portion of the optical fiber 101, the optical fiber 102, and the housing 103, which are at least a portion of the beam profile converter 100, are inserted into a lumen of the catheter body 81. In addition, the optical element 82 is arranged in the lumen of the catheter body 81 in the vicinity of the laser beam output window 81a, and is optically connected to the optical fiber 102 of the beam profile converter 100.

Figure 13:
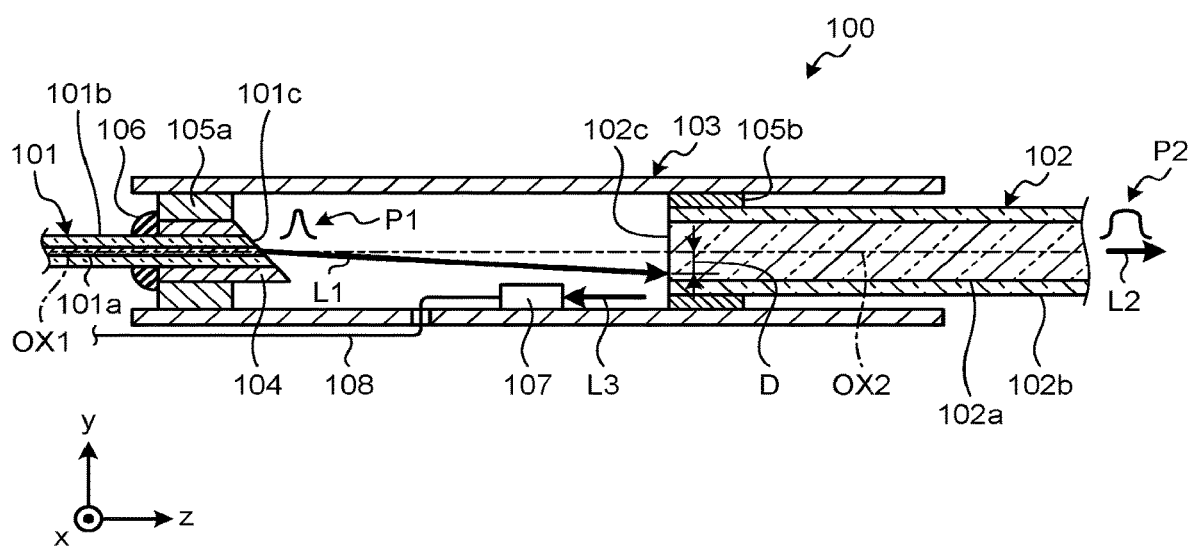
FIG. 13 is a schematic view illustrating a schematic configuration of a main part of a beam profile converter.

FIG. 13 is a schematic view illustrating a schematic configuration of a main part of the beam profile converter 100. The beam profile converter 100 includes a ferrule 104, fiber fixing members 105a and 105b, a resin 106, a light receiving element 107, and an electric wire 108, in addition to the optical fiber 101, the optical fiber 102, and the housing 103.

The optical fiber 101, which is a first optical fiber, is a single mode or multi-mode optical fiber including a core portion 101a and a cladding portion 101b. The optical fiber 101 is, for example, a step index type or graded index type multi-mode optical fiber, but is not particularly limited. The optical fiber 101 has, for example, a core diameter of 105 µm, a clad diameter of 125 µm, and a numerical aperture (NA) of 0.15, but is not particularly limited.

The optical fiber 101 has an end surface 101c as a first end surface. The end surface 101c is parallel to an x-axis and is inclined with respect to an optical axis OX1 of the optical fiber 101 which is a central axis of the core portion 101a and extends in a z direction. That is, the optical fiber 101 is a so-called diagonally cut one. The optical fiber 101 outputs a guided laser beam L1 from the end surface 101c.

The optical fiber 102, which is a second optical fiber, is a multi-mode optical fiber including a core portion 102a and a cladding portion 102b. The optical fiber 102 is, for example, a step index type or graded index type multi-mode optical fiber, but is not particularly limited. A core diameter of the optical fiber 102 is larger than the core diameter of the end surface 101c of the optical fiber 101, for example, 1.5 times or more. The optical fiber 102 has, for example, a core diameter of 400 µm, a clad diameter of 440 µm, and an NA of 0.22, but is not particularly limited.

The optical fiber 102 has an end surface 102c as a second end surface. The end surface 102c is orthogonal to an optical axis OX2 of the optical fiber 102 which is a central axis of the core portion 102a and extends in the z direction, and is parallel to the x-y plane. Note that the core portion 102a may be exposed on the end surface 102c, or may be in a state where a lens, a transmission film or the like is further provided on a surface of the end surface 102c. In addition, the end surface 102c is not limited to a flat shape, and may be a non-planar shape such as a convex shape or a concave shape. In the optical fiber 102, the laser beam L1 output from the end surface 101c of the optical fiber 101 is input to the core portion 102a of the end surface 102c, and the laser beam L1 is guided. The guided laser beam L1 is output to an optical element 82 as a laser beam L2. The optical element 82 collects the laser beam L2, bends an optical path, and outputs the laser beam L2 from the laser beam output window 81a of the catheter body 81.

Here, in a clad diameter $\Phi_1$ at the end surface 101c of the optical fiber 101 and a core diameter $\Phi_2$ at the end surface 102c of the optical fiber 102, a distance D between an input position of the light output from the end surface 101c to the end surface 102c of the optical fiber 102 and the optical axis OX2 of the optical fiber 102 is preferably expressed by the following equation (1).

$$(\Phi_2-\Phi_1)/2 > D \geq \Phi_1/2 \tag{1}$$

Specifically, when the clad diameter $\Phi_1$ at the end surface 101c of the optical fiber 101 is 125 µm and the core diameter of the optical fiber 102 is 400 µm, the equation (1) is $(400-125)/2=135.5 > D \geq 125/2=62.5$. Therefore, the distance D from the optical axis is preferably 62.5 µm or more and 135.5 µm or less.

The housing 103 is, for example, a cylindrical body, and accommodates an end portion including the end surface 101c of the optical fiber 101 and an end portion including the end surface 102c of the optical fiber 102. In addition, the housing 103 has a function of shielding and absorbing stray light, which is a component of the laser beam L1 that is not coupled to the core portion 102a of the optical fiber 102, and preventing the light from leaking to the outside. The housing 103 is preferably made of a material having high thermal conductivity, such as aluminum, in order to efficiently dissipate heat generated by the absorbed stray light.

The ferrule 104 is, for example, a cylindrical body made of zirconia, in which an optical fiber 101 is inserted and fixed, and one end side is diagonally cut so as to be flush with the end surface 101c. The fiber fixing member 105a is, for example, a cylindrical body made of metal, and the optical fiber 101 is fixed to the housing 103 via a ferrule 104. The resin 106 fixes the ferrule 104 and the fiber fixing member 105a. The fiber fixing member 105b is, for example, a cylindrical body made of metal, and fixes the optical fiber 102 to the housing 103. By fixing the optical fiber 101 and the optical fiber 102 to the housing 103, a relative positional relationship between the optical fiber 101 and the optical fiber 102 is fixed. In the modified example 1, the optical axis OX1 of the optical fiber 101 and the optical axis OX2 of the optical fiber 102 coincide with each other.

The light receiving element 107 is configured by, for example, a photodiode, receives stray light L3 which is a portion of the stray light described above, and outputs a current signal corresponding to a light receiving intensity to the electric wire 108. The electric wire 108 is connected to the monitor device 1004 as illustrated in FIG. 12. The monitor device 1004 has a function of receiving a current signal and monitoring the intensity of the laser beam L1 based on the current signal. In addition, the monitor device 1004 has a function of outputting a predetermined control signal to the laser light source 1001 based on the intensity of the monitored laser beam L1.

Figure 14:
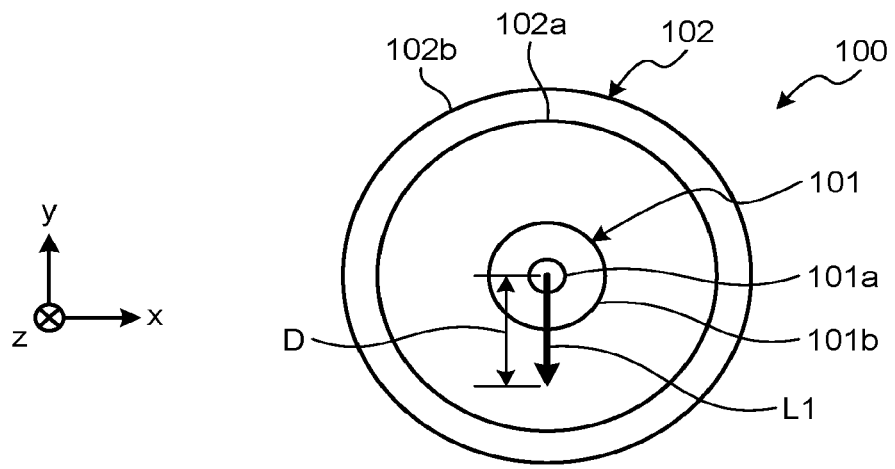
FIG. 14 is a view illustrating an input/output state of laser beam.

FIG. 14 is a view illustrating an input/output state of a laser beam, and is a view of the optical fibers 101 and 102 of FIG. 13 viewed from a negative direction of the z-axis. The optical fiber 101 outputs the guided laser beam L1 input from the laser light source 1001 from the end surface 101c. The end surface 101c is inclined with respect to the optical axis OX1. As a result, the laser beam L1 output from the end surface 101c travels in a direction inclined from the optical axis OX1 in a plane parallel to a y-z plane due to a difference in refractive index between the core portion 101a and a space inside the housing 103. Note that the beam profile P1 of the laser beam L1 is assumed to have a Gaussian shape.

The end surface 101c and the end surface 102c are non-parallel and are separated by an appropriate distance (for example, 100 µm or less on the optical axis). In addition, the core diameter of the optical fiber 102 is larger than the core diameter of the end surface 101c of the optical fiber 101. As a result, the laser beam L1 output from the end surface 101c is input to the core portion 102a of the end surface 102c with low loss. When the laser beam L1 is input, it is input in a direction inclined with respect to the end surface 102c at a position separated from the optical axis OX2 of the optical fiber 102 by a distance D. In this case, the laser beam L1 output from the end surface 101c is inclined with respect to the optical axis OX2 of the optical fiber 102 immediately before and immediately after being input to the core portion 102a of the end surface 102c at a position separated from the optical axis OX2 of the optical fiber 102.

While the optical fiber 102, which is a multi-mode optical fiber, guides the laser beam L1, a Gaussian-shaped beam profile component that is guided as a meridional ray, and a donut-shaped beam profile component that is guided as a skew ray are generated from the laser beam L1. As a result, the laser beam L2 output by the optical fiber 102 is a laser beam having a top hat-shaped beam profile P2 by mixing the meridional ray and the skew ray. That is, the optical fiber 102 functions as an optical fiber that converts a beam profile.

At this time, the skew ray is further generated at a relatively short waveguide distance by inputting the laser beam L1 to the core portion 102a of the end surface 102c in a direction inclined with respect to the end surface 102c at a position (offset position) where the laser beam L1 output from the end surface 101c is separated from the optical axis OX2 of the optical fiber 102. As a result, the optical fiber 102 can efficiently perform beam profile conversion. Furthermore, since this makes it possible to shorten a usage length of the relatively expensive optical fiber 102 due to its large diameter or large NA, a low-cost and efficient beam profile converter 100 can be realized. In addition, the beam profile converter 100 does not use a special optical fiber or an additional special optical element, and is realized by a simple configuration. In addition, preferably, if the core diameter of the optical fiber 102 is 1.5 times or more larger than the core diameter of the end surface 101c of the optical fiber 101, the loss is lower and the beam profile conversion can be performed with the shorter optical fiber 102.

In addition, such a simple configuration, low cost, and efficient beam profile converter 100 can be applied to a catheter 8 that is generally discarded after each use to realize a low cost catheter 8.

Note that in such a beam profile converter 100, the optical axis OX1 and the optical axis OX2 are made to match, and the end surface 101c and the end surface 102c are made non-parallel, so that an input state in which the laser beam L1 is input in a direction inclined with respect to the end surface 102c is realized at a position where the laser beam L1 is separated from the optical axis OX2. However, the configuration of the beam profile converter 100 can be modified so that the above-mentioned input state is realized. For example, the optical axis OX1 and the optical axis OX2 do not have to match, or the optical axis OX1 and the optical axis OX2 may be non-parallel.

In addition, by appropriately adjusting the inclination angle of the end surface 101c with respect to the optical axis OX1, the distance between the end surface 101c and the end surface 102c, and the combination of the core diameter and refractive index of the core portion 101a and the core diameter and refractive index of the core portion 102a, the beam profile of the laser beam L2 can be adjusted by adjusting the ratio of the meridional ray component to the skew ray component. For example, a top hat shape close to a Gaussian shape or a top hat shape close to a donut shape can be used. The top hat shape is a profile similar to or substantially similar to a super Gaussian shape having an order m of 3 or more. A field U of Super Gaussian is expressed by the following equation. Note that ω0 is a spot radius and r is a distance from a center.

$$U=\exp[-(r/\omega 0)^m]$$

In addition, in the modified example 1, the configuration in which the beam profile converter 100 is included in the catheter 8 has been described, but the laser device 1000 is not limited thereto. That is, the position where the beam profile converter 100 is provided may be between the connection portion 1003 and the laser light source 1001. As described above, since the beam profile converter 100 is provided on the laser light source 1001 side of the connection portion 1003, the beam profile converter 100 can be reused even when the catheter 8 is thrown away.

In addition, further modified examples (modified examples 2 to 5) of the modified example 1 of each of the above-described embodiments can be configured. Further modified examples will be described with reference to FIGS. 15 to 18.

MODIFIED EXAMPLE 2

Figure 15:
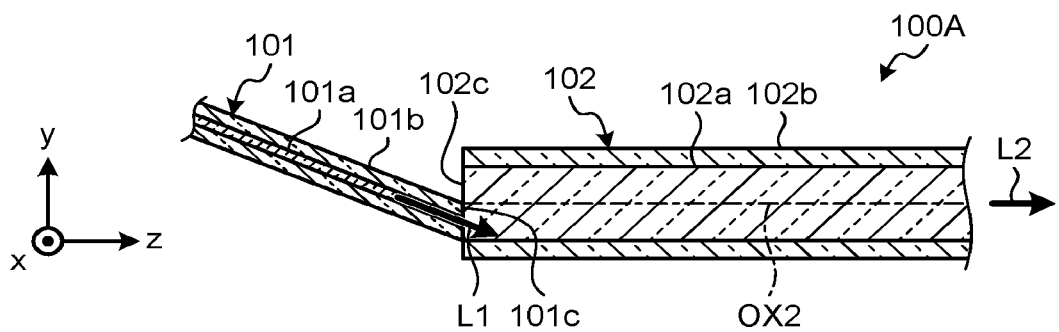
FIG. 15 is a schematic view illustrating a schematic configuration of a main part of a beam profile converter according to a modified example 2 of each embodiment.

FIG. 15 is a schematic view illustrating a schematic configuration of a main part of a beam profile converter in a modified example 2 of each embodiment. In a beam profile converter 100A of the modified example 2, the end surface 101c of the diagonally cut optical fiber 101 and the end surface 102c of the optical fiber 102 are fused and connected. At this time, an optical axis (not illustrated) of the optical fiber 101 and the optical axis OX2 of the optical fiber 102 are separated from each other in the y direction on a fusion connection surface. As a result, the end surface 101c and the end surface 102c are parallel to each other, but the optical axis of the optical fiber 101 and the optical axis OX2 of the optical fiber 102 are inclined to each other in a surface parallel to the y-z plane.

The beam profile converter 100A realizes an input state in which the laser beam L1 is input in a direction inclined with respect to the end surface 102c at a position separated from the optical axis OX2. Therefore, the beam profile converter 100A has the same effects of simple configuration, low cost, and efficiency as the beam profile converter 100.

Here, when fusing optical fibers having different outer diameters, reflected return light is incident on the cladding of the optical fiber on the input side, which causes the resin and the like to generate heat. Therefore, in order to suppress the heat generation of the resin or the like, it is desirable to provide a heat radiating portion on a fusion portion side of a coating portion of the optical fiber on the input side. The heat radiating portion is formed by applying, for example, heat radiating silicone.

MODIFIED EXAMPLE 3

Figure 16:
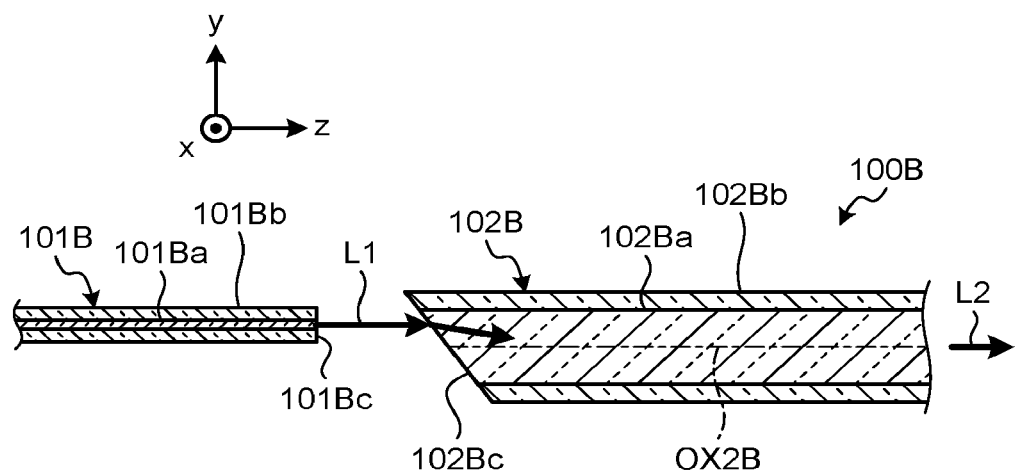
FIG. 16 is a schematic view illustrating a schematic configuration of a main part of a beam profile converter according to a modified example 3 of each embodiment.

FIG. 16 is a schematic diagram illustrating a schematic configuration of a main part of a beam profile converter in a modified example 3 of each embodiment. A beam profile converter 100B includes an optical fiber 101B and an optical fiber 102B.

The optical fiber 101B, which is a first optical fiber, includes a core portion 101Ba and a cladding portion 101Bb having the same configuration as the corresponding elements in the optical fiber 101. The optical fiber 101B has an end surface 101Bc as a first end surface. The end surface 101Bc is orthogonal to an optical axis (not illustrated) of the optical fiber 101B extending in the z direction and is parallel to the x-y plane.

The optical fiber 102B, which is a second optical fiber, includes a core portion 102Ba and a cladding portion 102Bb having the same configuration as the corresponding elements in the optical fiber 102. The optical fiber 102B has an end surface 102Bc as a second end surface. The end surface 102Bc is parallel to the x axis and is inclined with respect to an optical axis OX2B of the optical fiber 102B extending in the z direction. That is, the optical fiber 102B is a so-called diagonally cut one. In addition, the end surface 101Bc and the end surface 102Bc are not parallel to each other. In addition, the optical axis of the optical fiber 101B and the optical axis OX2B of the optical fiber 102B are parallel to each other, but separated in the y direction.

In the beam profile converter 100B, the optical fiber 101B outputs a guided laser beam L1 from the end surface 101Bc. The laser beam L1 output from the end surface 101Bc travels in the z direction.

Since a core diameter of the optical fiber 102B is larger than a core diameter of the optical fiber 101B, the laser beam L1 output from the end surface 101Bc is input to a core portion 102Ba of the end surface 102Bc at a position separated from the optical axis OX2B. Here, the end surface 102Bc is inclined with respect to the z axis. As a result, due to a difference in refractive index between the core portion 102Ba and the space inside the housing 103, the laser beam L1 input from the end surface 102Bc is input in a direction inclined from the optical axis OX2B in a plane parallel to the y-z plane on the end surface 102Bc. That is, the laser beam L1 output from the optical fiber 101B is parallel to the optical axis OX2B of the optical fiber 102B until immediately before being input to the core portion 102Ba, but is refracted in a direction inclined with respect to the optical axis OX2B of the optical fiber 102B after being input to the core portion 102Ba of the end surface 102Bc at a position separated from the optical axis OX2B of the optical fiber 102B. As a result, in the beam profile converter 100B, the optical fiber 102B functions as an optical fiber for converting the beam profile and outputs the laser beam L2, as in the case of the beam profile converter 100. As a result, the beam profile converter 100B can perform beam profile conversion at low cost and efficiently with a simple configuration.

It is only necessary to realize an input state in which the laser beam L1 is input in the direction inclined with respect to the end surface 102Bc at the position separated from the optical axis OX2B. Therefore, the configuration of the beam profile converter 100B may be modified so that the optical axis of the optical fiber 101B and the optical axis OX2B are not parallel to each other.

In addition, by appropriately adjusting the inclination angle of the end surface 102Bc with respect to the optical axis OX2B, the distance between the end surface 101Bc and the end surface 102Bc, and the combination of the core diameter and refractive index of the core portion 101Ba and the core diameter and refractive index of the core portion 102Ba, the beam profile of the laser beam L2 can be adjusted.

MODIFIED EXAMPLE 4

Figure 17:
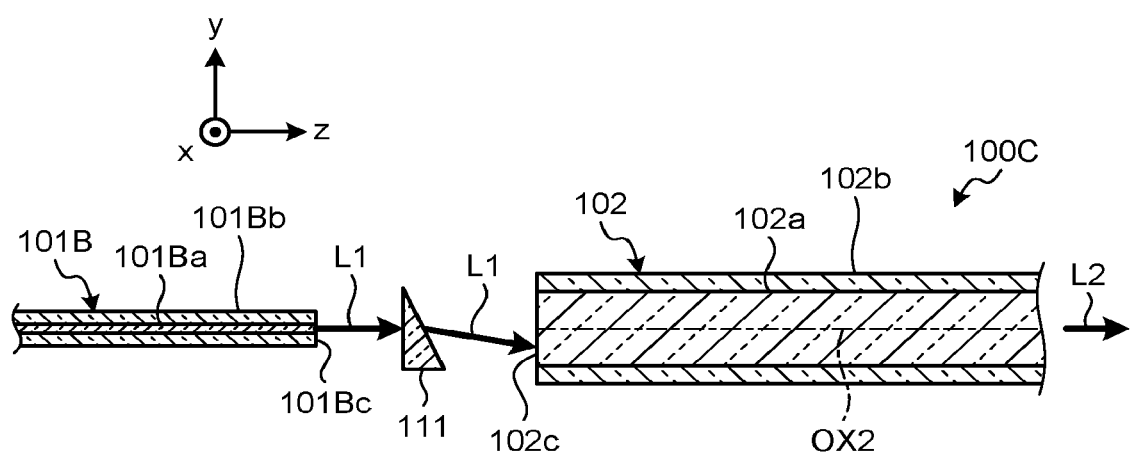
FIG. 17 is a schematic view illustrating a schematic configuration of a main part of a beam profile converter according to a modified example 4 of each embodiment.

FIG. 17 is a schematic view illustrating a schematic configuration of a main part of a beam profile converter in a modified example 4 of each embodiment. A beam profile converter 100C of the modified example 4 includes the optical fiber 101B and the optical fiber 102, and has a configuration in which a triangular prism 111 is arranged between the end surface 101Bc of the optical fiber 101B and the end surface 102c of the optical fiber 102.

In the beam profile converter 100C, the optical fiber 101B outputs a guided laser beam L1 from the end surface 101Bc. The laser beam L1 output from the end surface 101Bc travels in the z direction and is input to the triangular prism 111. The triangular prism 111 is an example of an optical element that refracts the laser beam L1, and refracts the laser beam L1 so that the traveling direction of the laser beam L1 is inclined from the z axis in a surface parallel to the y-z plane. As a result, the laser beam L1 is input to the core portion 102a of the end surface 102c of the optical fiber 102 at a position separated from the optical axis OX2, and is input to a direction inclined from the optical axis OX2 in the surface parallel to the y-z plane at the end surface 102c. As a result, the optical fiber 102 outputs the laser beam L2 whose beam profile has been converted. As a result, the beam profile converter 100C can perform beam profile conversion at low cost and efficiently with a simple configuration as in the case of the beam profile converter 100.

The triangular prism 111 may be provided in contact with the end surface 102c of the optical fiber 102. In this case, the laser beam L1 output from the end surface 101Bc of the optical fiber 101B is parallel to the optical axis OX2 of the optical fiber 102 until immediately before being input to the triangular prism 111, but is refracted by the triangular prism 111 and is inclined with respect to the optical axis OX2 when being input to the core portion 102a of the end surface 102c. In addition, the triangular prism 111 may be provided in contact with the end surface 101Bc of the optical fiber 101B. Even in this case, the laser beam L1 is input in a direction inclined from the optical axis OX2 immediately after being input to the core portion 102a of the end surface 102c.

MODIFIED EXAMPLE 5

Figure 18:
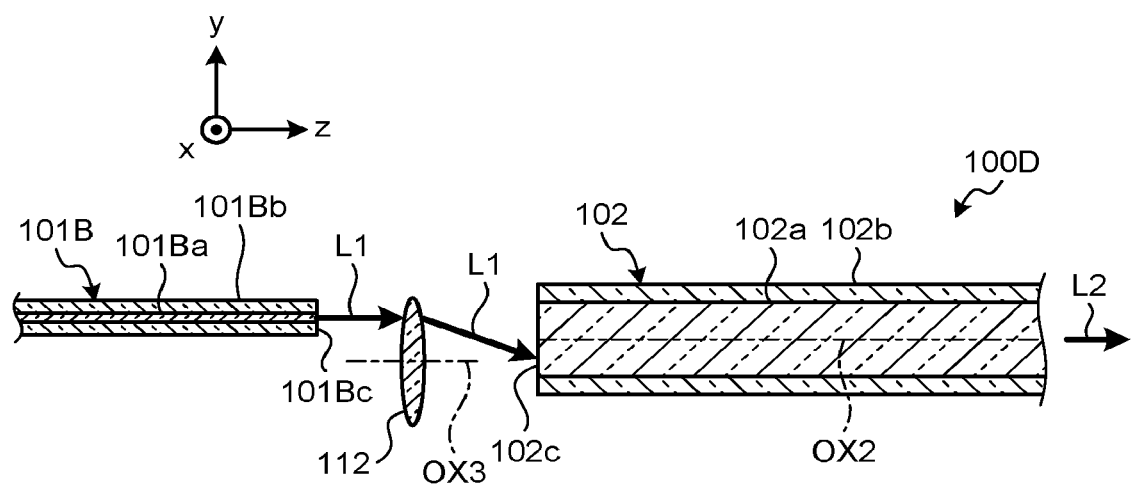
FIG. 18 is a schematic view illustrating a schematic configuration of a main part of a beam profile converter according to a modified example 5 of each embodiment.

FIG. 18 is a schematic view illustrating a schematic configuration of a main part of a beam profile converter according to a modified example 5 of each embodiment. A beam profile converter 100D of the modified example 5 has a configuration in which the triangular prism 111 is replaced with a lens 112 which is an example of an optical element that refracts the laser beam L1, in the configuration of the beam profile converter 100C of the modified example 4.

The lens 112 is arranged between the end surface 101Bc and the end surface 102c so that an optical axis OX3 does not match with either the optical axis of the optical fiber 101B or the optical axis OX2 of the optical fiber 102. As a result, as in the case of the beam profile converter 100C, the laser beam L1 output from the end surface 101Bc is refracted by the lens 112 so that the traveling direction of the laser beam L1 is inclined from the z axis in the surface parallel to the y-z plane. As a result, the laser beam L1 is input to the core portion 102a of the end surface 102c of the optical fiber 102 at a position separated from the optical axis OX2, and is input to a direction inclined from the optical axis OX2 in the surface parallel to the y-z plane at the end surface 102c. As a result, the optical fiber 102 outputs the laser beam L2 whose beam profile has been converted. As a result, the beam profile converter 100D can perform beam profile conversion at low cost and efficiently with a simple configuration as in the case of the beam profile converter 100.

The lens 112 may be provided in contact with the end surface 102c of the optical fiber 102. In this case, the laser beam L1 output from the end surface 101Bc of the optical fiber 101B is parallel to the optical axis OX2 of the optical fiber 102 until immediately before being input to the lens 112, but is refracted by the lens 112 and is inclined with respect to the optical axis OX2 when being input to the core portion 102a of the end surface 102c. In addition, the lens 112 may be provided in contact with the end surface 101Bc of the optical fiber 101B. Even in this case, the laser beam L1 is input in a direction inclined from the optical axis OX2 when it is input to the core portion 102a of the end surface 102c.

According to the present disclosure, it is possible to appropriately irradiate a laser beam toward an irradiation target located lateral to an insertion direction, such as in a small-diameter tube, and to detect breakage of an optical fiber.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. A medical laser probe comprising:
   an optical probe comprising:
      an optical fiber that propagates light of a plurality of wavelengths introduced from a plurality of light sources;
      a reflecting portion that is provided on the optical fiber, transmits a laser beam of a first wavelength of the plurality of wavelengths and reflects light of a second wavelength of the plurality of wavelengths; and
      a traveling direction changing portion that is provided on a distal end side of the optical fiber and changes a traveling direction of the laser beam of the first wavelength that has transmitted through the reflecting portion to a direction different from a traveling direction before transmitting through the reflecting portion, wherein the traveling direction changing portion is configured by a bending structure having a structure in which a portion on the distal end side of the optical fiber is bent, and the reflecting portion is provided closer to a proximal end side of the optical fiber than the bending structure; and a catheter that is to be inserted into a blood vessel, wherein:

the optical fiber has a size that is insertable into the blood vessel and is inserted inside the catheter, the laser beam of the first wavelength is a cauterizing laser beam, the light of the second wavelength is a monitor light for detecting breakage, and the traveling direction changing portion irradiates the cauterizing laser beam from a distal end surface of the optical fiber toward a blood vessel wall.

2. The medical laser probe according to claim 1, wherein the reflecting portion is a fiber Bragg grating formed on the optical fiber.

3. The medical laser probe according to claim 1, wherein the reflecting portion is a reflective film provided in a slit formed in the optical fiber.

4. The medical laser probe according to claim 3, comprising a protective material for protecting the optical fiber, wherein the reflective film is fixed to the optical fiber by the protective material.

5. The medical laser probe according to claim 1, wherein the reflecting portion is a reflective film provided on the distal end surface of the optical fiber, the traveling direction changing portion is configured by a side irradiation mechanism provided in front of the distal end surface in an extending direction of the optical fiber, and the side irradiation mechanism includes a reflecting surface that reflects a traveling direction of the laser beam emitted from the distal end surface in a direction inclined at a predetermined angle with respect to the extending direction of the optical fiber.

6. The medical laser probe according to claim 5, comprising a light transmitting member provided in the protective material of the optical fiber, wherein the light reflected by the reflecting surface of the side irradiation mechanism transmits through the light transmitting member.

7. The medical laser probe according to claim 1, wherein the reflecting portion is configured to reflect a third wavelength, which is different from the first wavelength and the second wavelength, in addition to the second wavelength.

8. The medical laser probe according to claim 7, wherein light of the third wavelength is a monitor light for estimating a bending amount, and the traveling direction changing portion irradiates the cauterizing laser beam from the distal end surface of the optical fiber toward a blood vessel wall.

9. The medical laser probe according to claim 7, wherein the third wavelength is in a range of 800 nm to 2000 nm.

10. The medical laser probe according to claim 1, wherein the second wavelength is in a range of 400 nm to 800 nm.

11. A cauterization device comprising:

the medical laser probe according to claim 1;

a plurality of light sources that emit light of a plurality of wavelengths introduced into the optical fiber;

a multiplexer that optically connects the plurality of light sources and the optical fiber;

a monitor portion that monitors reflected light of the light of the second wavelength reflected by the reflecting portion;

a connection portion that connects the medical laser probe and the multiplexer, wherein the light sources include a cauterizing light source that generates the cauterizing laser beam, and a monitor light source that generates the monitor light.

12. The cauterization device according to claim 11, wherein the connection portion is configured by parts removable and replaceable from the medical laser probe and the multiplexer.

13. The cauterization device according to claim 11, wherein the connection portion is configured by spatial coupling.

14. The cauterization device according to claim 11, wherein power of a laser beam passing through the connection portion is 100 W or less.

15. The cauterization device according to claim 11, wherein the power of the laser beam passing through the connection portion is in a range of 1 W to 30 W.

16. The cauterization device according to claim 11, wherein the reflecting portion reflects a third wavelength, which is different from the first wavelength and the second wavelength, in addition to the second wavelength, the monitor portion monitors reflected light of light of the second wavelength and light of the third wavelength reflected by the reflecting portion, and the plurality of light sources include a monitor light source that generates the monitor light.

17. The cauterization device according to claim 16, wherein power of the light of the second and third wavelengths is 5 mW or less.

18. The cauterization device according to claim 16, wherein the power of the light of the second wavelength and the third wavelength is 1 mW or less.

* * * * *